US009289147B2

(12) United States Patent
Tegg

(10) Patent No.: US 9,289,147 B2
(45) Date of Patent: Mar. 22, 2016

(54) MULTI-DIRECTIONAL FLEXIBLE WIRE HARNESS FOR MEDICAL DEVICES

(75) Inventor: Troy T. Tegg, Elk River, MN (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 712 days.

(21) Appl. No.: 13/465,655

(22) Filed: May 7, 2012

(65) Prior Publication Data

US 2012/0283570 A1  Nov. 8, 2012

Related U.S. Application Data

(63) Continuation-in-part of application No. 13/105,646, filed on May 11, 2011, now Pat. No. 8,676,290.

(60) Provisional application No. 61/333,641, filed on May 11, 2010, provisional application No. 61/621,814, filed on Apr. 9, 2012.

(51) Int. Cl.
*A61B 5/042* (2006.01)
*A61M 25/01* (2006.01)

(52) U.S. Cl.
CPC ............ *A61B 5/042* (2013.01); *A61M 25/0136* (2013.01); *A61M 25/0147* (2013.01)

(58) Field of Classification Search
CPC .......... H01B 7/04; H04R 17/00; H02N 2/025
See application file for complete search history.

(56) References Cited

U.S. PATENT DOCUMENTS

| D304,616 | S | 11/1989 | Dunlap et al. |
|---|---|---|---|
| 4,906,199 | A | 3/1990 | Twomey et al. |
| 4,924,092 | A | 5/1990 | Crist, Jr. |
| 4,944,727 | A | 7/1990 | McCoy |
| D312,306 | S | 11/1990 | Michelson |
| 5,108,368 | A | 4/1992 | Hammerslag et al. |
| 5,125,895 | A | 6/1992 | Buchbinder et al. |
| 5,125,896 | A | 6/1992 | Hojeibane |
| 5,170,803 | A | 12/1992 | Hewson et al. |
| 5,195,968 | A | 3/1993 | Lundquist et al. |

(Continued)

FOREIGN PATENT DOCUMENTS

| CN | 101351724 | 1/2009 |
|---|---|---|
| EP | 0431206 | 7/1995 |

(Continued)

OTHER PUBLICATIONS

Title: International Search Report & Written Opinion Citation: PCT/US2013/026990 Publication Date: Apr. 29, 2013.

(Continued)

*Primary Examiner* — Jeremy C Norris
*Assistant Examiner* — Muhammed Azam
(74) *Attorney, Agent, or Firm* — Dykema Gossett PLLC

(57) ABSTRACT

A wire harness for a medical device includes a wiring bundle, a distal flex circuit, and a proximal flex circuit. The wiring bundle includes a plurality of twisted pair wiring and a shield, and operatively or conductively connects the distal flex circuit to the proximal flex circuit. The distal flex circuit may be configured to operatively or conductively connect to an electrically controlled object located in a distal portion of the medical device. The proximal flex circuit may be configured to operatively or conductively connect to an electrical connector.

20 Claims, 7 Drawing Sheets

(56) References Cited

U.S. PATENT DOCUMENTS

| | | | |
|---|---|---|---|
| 5,203,772 | A | 4/1993 | Hammerslag et al. |
| 5,254,088 | A | 10/1993 | Lundquist et al. |
| 5,273,535 | A | 12/1993 | Edwards et al. |
| 5,318,525 | A | 6/1994 | West et al. |
| 5,325,845 | A | 7/1994 | Adair |
| 5,342,299 | A | 8/1994 | Snoke et al. |
| 5,354,297 | A | 10/1994 | Avitall |
| 5,383,852 | A | 1/1995 | Stevens-Wright |
| 5,397,304 | A | 3/1995 | Truckai |
| 5,415,633 | A | 5/1995 | Lazarus et al. |
| 5,487,757 | A | 1/1996 | Truckai et al. |
| 5,520,644 | A | 5/1996 | Imran |
| 5,531,721 | A | 7/1996 | Pepin et al. |
| 5,545,200 | A | 8/1996 | West et al. |
| 5,549,542 | A | 8/1996 | Kovalcheck |
| 5,662,606 | A | 9/1997 | Cimino et al. |
| D384,740 | S | 10/1997 | Musgrave et al. |
| 5,702,433 | A | 12/1997 | Taylor et al. |
| 5,715,817 | A | 2/1998 | Stevens-Wright et al. |
| 5,769,781 | A | 6/1998 | Chappuis |
| 5,842,984 | A | 12/1998 | Avitall |
| 5,853,409 | A | 12/1998 | Swanson et al. |
| 5,860,974 | A | 1/1999 | Abele |
| 5,861,024 | A | 1/1999 | Rashidi |
| 5,876,340 | A | 3/1999 | Tu et al. |
| 5,891,138 | A | 4/1999 | Tu et al. |
| 5,897,554 | A | 4/1999 | Chia et al. |
| 5,921,924 | A | 7/1999 | Avitall |
| 5,931,577 | A | 8/1999 | Ishibashi |
| 5,931,811 | A | 8/1999 | Haissaguerre |
| 5,938,616 | A | 8/1999 | Eaton |
| 5,941,845 | A | 8/1999 | Tu et al. |
| 5,944,690 | A | 8/1999 | Falwell et al. |
| 5,987,344 | A | 11/1999 | West |
| 6,066,125 | A | 5/2000 | Webster, Jr. |
| 6,068,629 | A | 5/2000 | Haissaguerre et al. |
| 6,071,274 | A | 6/2000 | Thompson et al. |
| 6,071,279 | A | 6/2000 | Whayne et al. |
| 6,076,012 | A | 6/2000 | Swanson et al. |
| 6,117,083 | A * | 9/2000 | Buck et al. .................. 600/459 |
| 6,198,974 | B1 | 3/2001 | Webster, Jr. |
| 6,211,936 | B1 | 4/2001 | Nakamura |
| 6,233,476 | B1 | 5/2001 | Strommer et al. |
| 6,241,727 | B1 | 6/2001 | Tu et al. |
| 6,308,091 | B1 | 10/2001 | Avitall |
| 6,330,473 | B1 | 12/2001 | Swanson et al. |
| D455,210 | S | 4/2002 | Henderson |
| 6,402,746 | B1 | 6/2002 | Whayne et al. |
| 6,423,059 | B1 | 7/2002 | Hanson et al. |
| 6,430,426 | B2 | 8/2002 | Avitall |
| 6,454,758 | B1 | 9/2002 | Thompson et al. |
| 6,464,645 | B1 | 10/2002 | Park |
| 6,497,667 | B1 | 12/2002 | Miller |
| 6,554,794 | B1 | 4/2003 | Mueller |
| 6,582,536 | B2 | 6/2003 | Shimada |
| 6,690,963 | B2 | 2/2004 | Ben-Haim et al. |
| 6,942,661 | B2 | 9/2005 | Swanson et al. |
| 7,130,700 | B2 | 10/2006 | Gardeski et al. |
| 7,197,354 | B2 | 3/2007 | Sobe |
| 7,263,397 | B2 | 8/2007 | Hauck et al. |
| D550,356 | S | 9/2007 | Anderson et al. |
| 7,386,339 | B2 | 6/2008 | Strommer et al. |
| 7,507,229 | B2 | 3/2009 | Hewitt et al. |
| 7,536,218 | B2 | 5/2009 | Govari et al. |
| D612,044 | S | 3/2010 | Scheibe et al. |
| 7,691,095 | B2 | 4/2010 | Bednarek |
| 7,715,204 | B2 | 5/2010 | Miller |
| 7,785,252 | B2 | 8/2010 | Danitz et al. |
| 7,848,789 | B2 | 12/2010 | Govari et al. |
| D634,421 | S | 3/2011 | El-Gad et al. |
| D634,422 | S | 3/2011 | El-Gad et al. |
| 7,901,358 | B2 | 3/2011 | Mehi |
| 8,072,119 | B2 * | 12/2011 | Engel .................. 310/322 |
| 8,123,721 | B2 | 2/2012 | Tegg |
| 8,137,308 | B2 | 3/2012 | Schultz |
| D695,891 | S | 12/2013 | Biel et al. |
| D696,397 | S | 12/2013 | Guarraia et al. |
| 8,620,399 | B2 | 12/2013 | Gonda |
| 8,676,290 | B2 | 3/2014 | Tegg et al. |
| 8,858,495 | B2 | 10/2014 | Tegg et al. |
| 2002/0077590 | A1 | 6/2002 | Ponzi et al. |
| 2002/0087166 | A1 | 7/2002 | Brock et al. |
| 2002/0087169 | A1 | 7/2002 | Brock et al. |
| 2003/0040684 | A1 | 2/2003 | Soukup et al. |
| 2004/0153049 | A1 | 8/2004 | Hewitt et al. |
| 2005/0038467 | A1 | 2/2005 | Hebert et al. |
| 2005/0082950 | A1 * | 4/2005 | Zakoji .................. 310/348 |
| 2005/0107737 | A1 | 5/2005 | McDaniel |
| 2005/0148878 | A1 | 7/2005 | Phelps et al. |
| 2005/0267461 | A1 | 12/2005 | Cao et al. |
| 2006/0142694 | A1 | 6/2006 | Bednarek et al. |
| 2006/0142695 | A1 | 6/2006 | Knudson |
| 2007/0276324 | A1 | 11/2007 | Laduca et al. |
| 2008/0234660 | A2 | 9/2008 | Cumming et al. |
| 2008/0312536 | A1 | 12/2008 | Dala-Krishna |
| 2009/0105640 | A1 | 4/2009 | Bednarek et al. |
| 2009/0264817 | A1 | 10/2009 | Flach et al. |
| 2010/0004591 | A1 | 1/2010 | Barenboym et al. |
| 2010/0004592 | A1 | 1/2010 | Butler |
| 2010/0130924 | A1 | 5/2010 | Martin et al. |
| 2010/0174233 | A1 | 7/2010 | Kuban et al. |
| 2010/0262075 | A1 | 10/2010 | Danitz et al. |
| 2010/0280449 | A1 | 11/2010 | Alvarez et al. |
| 2011/0264074 | A1 | 10/2011 | Tegg |
| 2011/0282176 | A1 | 11/2011 | Tegg |
| 2012/0029334 | A1 | 2/2012 | Tegg |

FOREIGN PATENT DOCUMENTS

| | | |
|---|---|---|
| GB | 2315020 | 1/1998 |
| JP | H08308833 | 11/1996 |
| JP | 2001104311 | 4/2001 |
| JP | 2005218518 | 8/2005 |
| WO | 98/33428 | 8/1998 |
| WO | 98/33429 | 8/1998 |
| WO | 2006/092016 | 9/2006 |
| WO | 2009/149315 | 10/2009 |

OTHER PUBLICATIONS

"Blazer II XP, Temperature Ablation Catheter, Extra Power . . . Controlled. Create larger, deeper lesions for exceptional outcomes in atrial flutter", *Boston Scientific Corporation* 2009 , 1-4.

"EZ Steer, Bi-Directional Catheters, "Micro Movements. Macro Control."", *Biosense Webster, a Johnson & Johnson Company* 2006 , 1-6.

Strole, Jeff et al., "A Novel Flex Circuit Area-Array Interconnect System for a Catheter-Based Ultrasound Transducer", Presented at IMAPS 2002 Denver, Colorado, Sep. 5, 2002.

Title: International Search Report & Written Opinion Citation: PCT/US2012/022678 Publication Date: May 30, 2012.

Author: Masson, Lucie Title: Tracking 3D objects using flexible models Citation: BMVC Publication Date: Sep. 2005.

Bennink, H.E.; "Warping a Neuro-Anatomy Atlas on 3D MRI Data with Radial Basis Functions"; In: Proc. Intern. Conf. on Biomedical Engineering (Biomed) 2006, Kuala Lumpur, Malaysia; Reference pp. 1-4; Publication Date: Dec. 11-14, 2006.

Bookstein, Fred L.; "Principal Warps: Thin-Plate Splines and the Decomposition of Deformations" Citation: IEEE Transactions on Pattern Analysis and Machine Intelligence; vol. 11, No. 6 Reference pp. 567-585; Publication Date: Jun. 1989.

Bors, Adrian G.; "Median Radial Basis Functions Neural Network"; Citation: IEEE Computational Intelligence Society, vol. 7, Issue 6 Reference pp. 1-33 Publication Date: Nov. 1996.

Carr, J.C.; "Reconstruction and Representation of 3D Objects with Radial Basis Functions"; Annual Conference of Computer Graphics SIGGRAPH; Reference pp. 67-76; Publication Date: Aug. 2001.

Chui, Haili; "A new algorithm for non-rigid point matching"; IEEE Conference on Computer Vision and pattern, vol. 2; Reference pp. 44-51; Publication Date: Jun. 2000.

(56) References Cited

OTHER PUBLICATIONS

Chui, Haili; "A new point matching algorithm for non-rigid registration"; Computer Vision and Understanding, vol. 89, Issues 2-3; Feb.-Mar. 2003.

Donato, Gianluca; "Approximate thin plate spline mappings"; Computer Vision—ECCV Lecture Notes in Computer Science, vol. 2352; Reference pp. 21-31; Publication Date: Apr. 2002.

Ebeling, H.; "ASMOOTH: A simple and efficient algorithm for adaptive kernel smoothing of two-dimensional imaging data"; Mon. Not. R. Astron. Soc., vol. 368; Reference pp. 65-73; Publication Date: May 2006.

International Search Report and Written Opinion in PCT Application No. PCT/US2013/045885 (Oct. 1, 2013).

Jain, Ameet Kumar; "FTRAC—A robust fluoroscope tracking fiducial"; Medical Physics, vol. 32, No. 10; Reference pp. 3185-3198; Publication Date: Oct. 2005.

Ju, Tao; "Mean Value Coordinates for Closed Triangular Meshes"; ACM Transactions on Graphics 24(3); Reference pp. 561-566; Publication Date: Jul. 2005.

Orr, Mark J; "Introduction to radial basis function networks"; Reference pp. 1-67; Publication Date: Apr. 1996.

Park, J.; "Universal approximation using radial-basis-function networks"; Neural Computation, vol. 3, No. 2; Reference Pages: Abstract; Publication Date: 1991.

Rajesh, Kabra et al., "Recent trends in imaging for atrial fibrillation ablation", Indian Pacing and Electrophysiology Journal, pp. 215-227, May 5, 2010.

Reinsch, Christian; "Smoothing by Spline Functions"; Citation: 13 Numer. Math. Bd. 10 Reference pp. 177-183 Publication Date: Oct. 1967.

Supplementary European Search Report in EP Application No. 12782484.5 (Sep. 12, 2014).

Supplementary Partial European Search Report in EP Application No. 12770539.0 (Dec. 4, 2014).

Title: Definition: interpolate Citation: Collins English Dictionary—Complete and Unabridged 10th Edition, 2009, Harper Collins Publishers Publication Date: 2009.

Title: International Search Report & Written Opinion Citation: PCT/US2012/030925 Publication Date: Jun. 20, 2012.

Wittkampf, Fred H.; "LocaLisa: New Technique for Real-Time 3-Dimensional localization of regular intracardiac electrodes"; Circulation—Journal of the American Heart Association; Reference pp. 1312-1317; Publication Date: Mar. 1999.

International Search Report and Written Opinion in PCT Application No. PCT/US2012/023292 (May 30, 2012).

Wiley, David F.; "Evolutionary Morphing"; Proceedings of IEEE Visualization; Reference pp. 431-438; Publication Date: Oct. 2005.

* cited by examiner

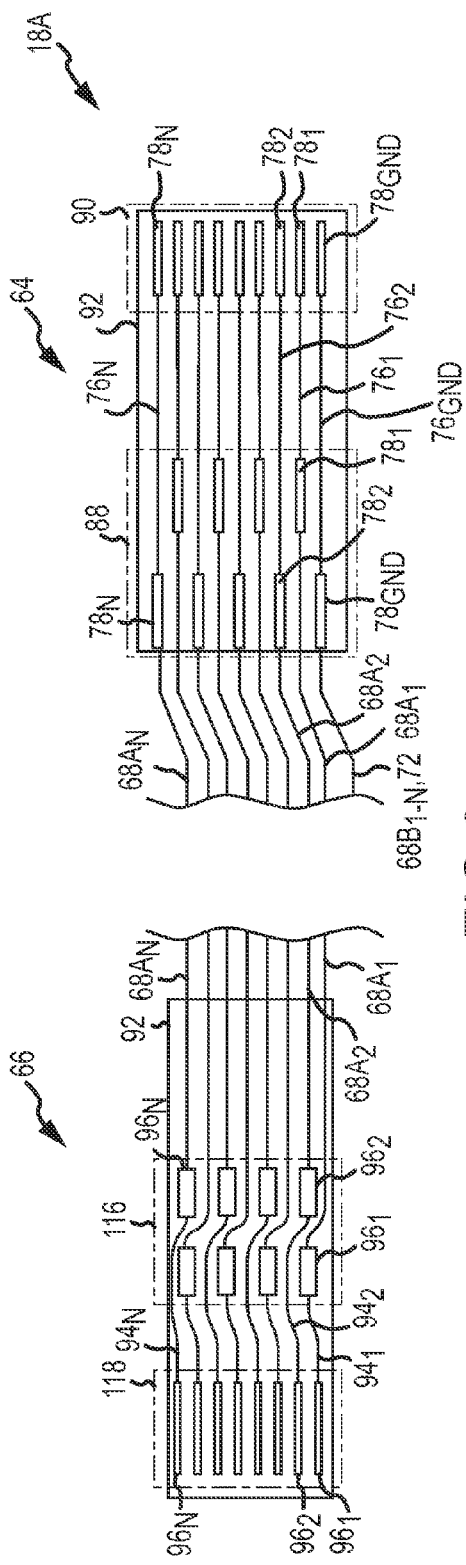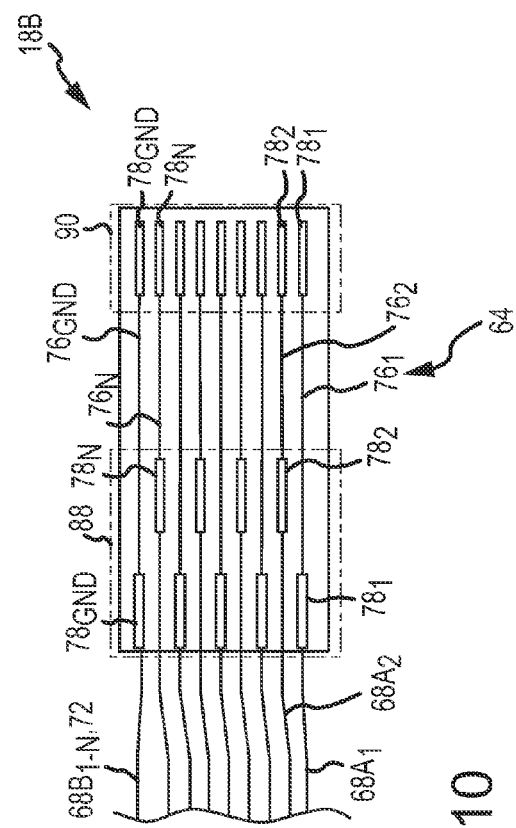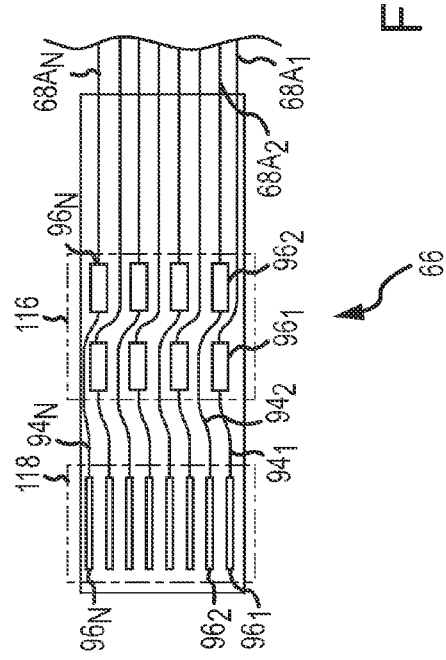
FIG.9   FIG.10

MULTI-DIRECTIONAL FLEXIBLE WIRE HARNESS FOR MEDICAL DEVICES

CROSS-REFERENCE TO RELATED APPLICATIONS

This application is a continuation-in-part of U.S. application Ser. No. 13/105,646, filed May 11, 2011 (the '646 application), which claims the benefit of U.S. provisional application No. 61/333,641, filed May 11, 2010 (the '641 application). This application also claims the benefit of U.S. Provisional Application No. 61/621,814, filed Apr. 9, 2012 (the '814 application). The '646 application, the '641 application, and the '814 application are all hereby incorporated by reference as though fully set forth herein.

BACKGROUND OF THE INVENTION a. Field of the Invention

This disclosure relates generally to the field of medical devices, including a medical device for introduction into a body, such as a catheter, and other maneuverable medical devices.

b. Background Art

Catheters and sheaths having flexible tubular bodies with deflectable distal ends and control handles for controlling distal end deflection are commonly used in connection with many noninvasive medical procedures. For example, catheters having one or more ultrasound transducers along the distal ends of their bodies are used for intra-cardiac echocardiography studies. The distal end of the catheter body is typically positioned in a patient's heart and an ultrasound transducer may provide signal data which may be used to generate images to visualize cardiac structures and blood flow within the heart during intra-cardiac visualization, navigation, and mapping. Generally, an ultrasound transducer may comprise one piezoelectric element or a plurality of piezoelectric elements. Each piezoelectric element may have a relatively fine electrically conductive wire attached thereto and the wire may extend through the catheter body, ultimately to an electronic control unit (ECU). For example, the conductive wire may extend from the distal end to a proximal end of the catheter where the wire may be terminated with an electrical connector that can be configured to connect with a corresponding socket provided in an ECU. To organize a plurality of wires running throughout the catheter body, the wires may be positioned and attached on a flat mylar ribbon.

In an effort to obtain sharper images, ultrasound transducers having an increased number of elements may be utilized. However, an increased number of elements can also increase the number of associated or corresponding conductive wires extending through the catheter body. An increased number of conductive wires extending through the catheter body may decrease the flexibility and maneuverability of the catheter by increasing the stiffness associated with the wiring. Further, when wiring is provided on flat ribbons, the amount of flexibility may be inconsistent depending on the direction of the flex or bend of the body relative to the position of the ribbon.

The foregoing discussion is intended only to illustrate the present field and should not be taken as a disavowal of claim scope.

BRIEF SUMMARY OF THE INVENTION

In an embodiment, a wire harness for a medical device may comprise a wiring bundle, a distal flex circuit, and a proximal flex circuit. The wiring bundle may comprise a plurality of twisted pair wiring (or twisted wire pairs) and a shield surrounding a portion of the plurality of twisted pair wiring, and may operatively or conductively connect a distal flex circuit to a proximal flex circuit. The distal flex circuit may be configured to operatively or conductively connect to an electrically controlled object located in a distal portion of the medical device. The proximal flex circuit may be configured to operatively or conductively connect to an electrical connector. The medical device may comprise an elongate tubular body having a lumen and the wire harness may run substantially throughout the lumen of the elongate tubular body of the medical device.

In an embodiment, a pair of wire harnesses for a medical device may comprise a first wire harness and a second wire harness, where each wire harness may comprise a wiring bundle, a distal flex circuit, and a proximal flex circuit. The wiring bundle may comprise a plurality of twisted pair wiring and a shield surrounding a portion of the plurality of twisted pair wiring, and may operatively or conductively connect a distal flex circuit to a proximal flex circuit. The distal flex circuit may be configured to operatively or conductively connect to an electrically controlled object assembly comprising an electrically controlled object and at least one flexible printed circuit. The electrically controlled object assembly may be located in a distal portion of the medical device. The proximal flex circuit may be configured to operatively or conductively connect to an electrical connector. The first wire harness and the second wire harness may be each operatively or conductively connected to the same flexible printed circuit of the electrically controlled object assembly.

In an embodiment, a plurality of wire harness pairs for a medical device may comprise a wire harness pair comprising a first wire harness and a second wire harness. Each wire harness may comprise a wiring bundle, a distal flex circuit, and a proximal flex circuit. The wiring bundle may comprise a plurality of twisted pair wiring and a shield surrounding a portion of the plurality of twisted pair wiring. The distal flex circuit may be configured to operatively or conductively connect to an ultrasound transducer assembly. The ultrasound transducer assembly may comprise an ultrasound transducer and a plurality of flexible printed circuits operatively or conductively connected to the ultrasound transducer. The ultrasound transducer assembly may be located in a distal portion of the medical device. The proximal flex circuit may be configured to operatively or conductively connect to an electrical connector which may be configured to operatively or conductively connect to an electronic control unit. The first wire harness and the second wire harness may be each operatively or conductively connected to the same flexible printed circuit of the plurality of flexible printed circuits of the ultrasound transducer assembly.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 9 is a general illustration of an embodiment of a distal flex circuit and a proximal flex circuit of the wire harness of FIG. 5.

FIG. 10 is a general illustration of another embodiment of a distal flex circuit and a proximal flex circuit of the wire harness of FIG. 5.

DETAILED DESCRIPTION OF THE INVENTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting or absolute.

Figure 1:
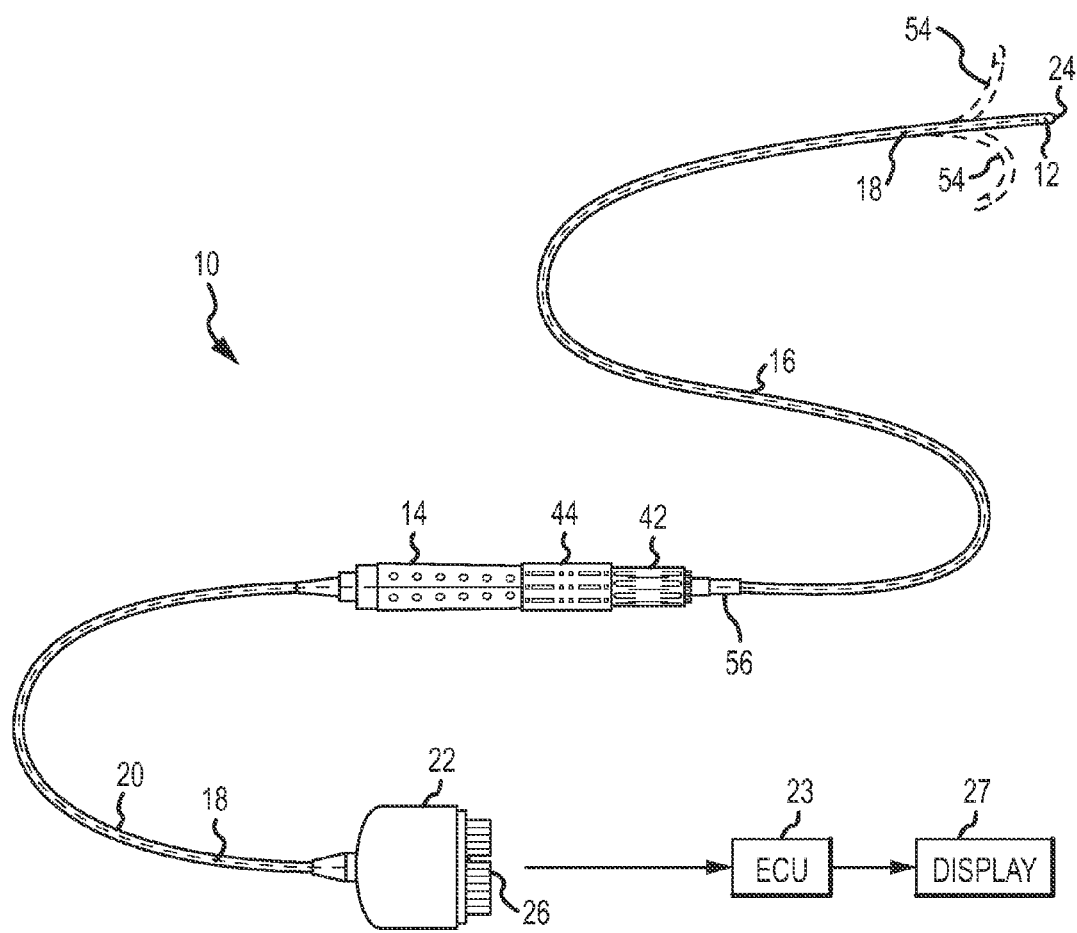
FIG. 1 generally illustrates a diagrammatic view of a system including an embodiment of a catheter connected to an electronic control unit (ECU) and a display.
Figure 2:
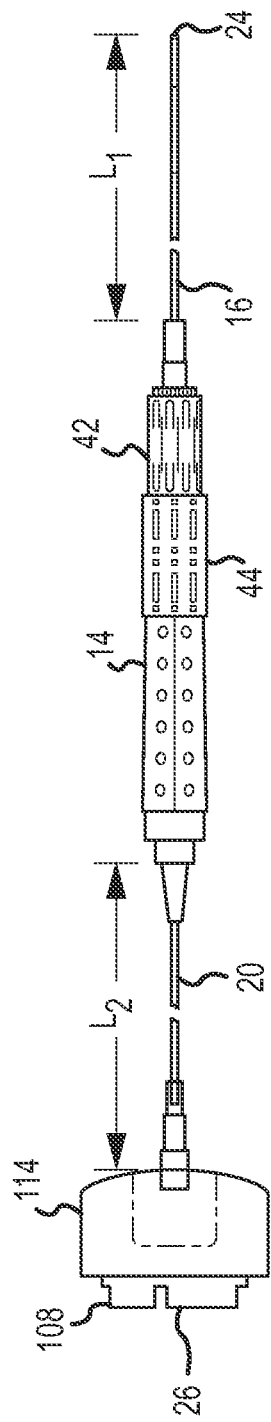
FIG. 2 generally illustrates a side view of the embodiment of the catheter having an ultrasound transducer assembly, body, handle, electrical connector, and wire harness of FIG. 1.

Referring now to the drawings wherein like reference numerals are used to identify identical components in the various views, FIGS. 1-2 generally illustrates an exemplary embodiment of a catheter 10 for performing one or more diagnostic and/or therapeutic functions. More particularly, the catheter 10 may include components for performing intracardiac echocardiography ("ICE") procedures. It should be understood, however, that while the description below is with respect to an ICE catheter, the subject matter of the disclosure may find application in connection with a variety of medical devices. As generally illustrated in FIG. 1, a catheter 10 may comprise an ultrasound transducer assembly 12, a handle 14, a body 16, a wire harness 18, a tubing 20, and an electrical connector 22 configured to connect to an electronic control unit (ECU) 23, such as, for example and without limitation, the ViewMate™ Z or ViewMate™ II intracardiac ultrasound consoles via the compatible ViewFlex™ Catheter Interface Module commercialized by St. Jude Medical, Inc. In an embodiment, the ultrasound console may have a system frequency of 4.5-8.5 MHz. In another embodiment, the system frequency may be 3.0-9.0 MHz. In an embodiment, the ultrasound console may have a viewing angle of 90° F. In another embodiment, the viewing angle may be 80° F. In an embodiment, the ultrasound consoles may have a maximum viewing depth of 18 cm. The catheter 10 may have a distal end 24 and a proximal end 26. In an embodiment, the ultrasound imaging modes may comprise a B-mode, M-mode, Spectral (Pulse Wave Doppler) Doppler, and/or Color Doppler.

Figure 3:
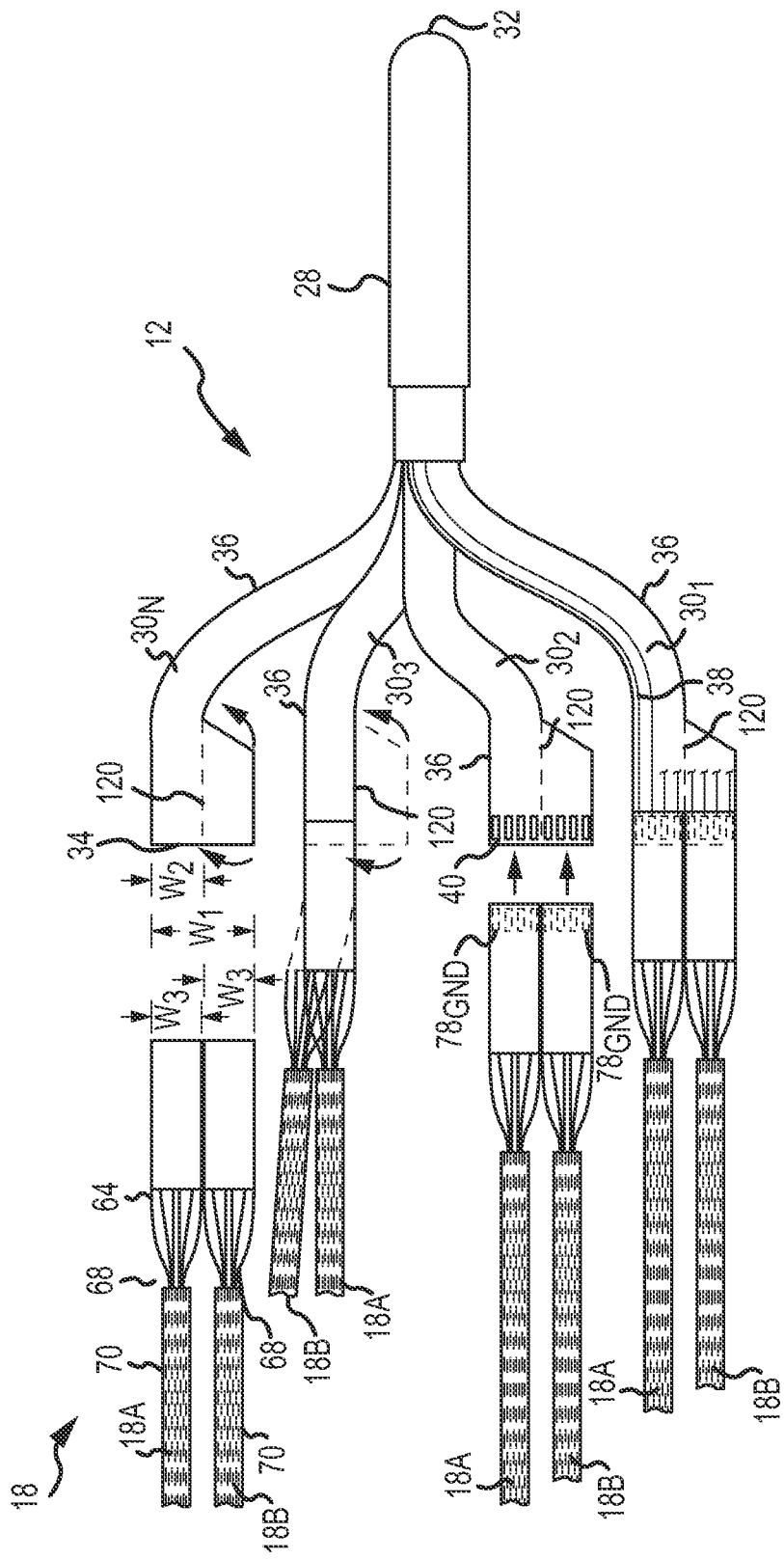
FIG. 3 is an illustration of an embodiment of an ultrasound transducer assembly in various configurations with a plurality of wire harnesses.

Referring to FIG. 3, an ultrasound transducer assembly 12 may comprise a transducer 28 and a plurality of flexible printed circuits 30. The ultrasound transducer assembly may have a distal end 32 and a proximal end 34. The transducer 28 may include a plurality of piezoelectric elements that are operatively or conductively connected to the flexible printed circuits 30. Each flexible printed circuit 30 may comprise a flexible substrate 36, a plurality of conductive traces 38 defined on the substrate 36, and a plurality of conductive pads 40. Each piezoelectric element may be operatively or conductively connected to a separate trace 38 defined on the substrate 36 of the flexible printed circuit 30. In an exemplary embodiment, the piezoelectric elements of the transducer may be operatively or conductively connected to the plurality of traces 38 by trace-to-trace soldering using techniques such as reflow (hot bar) soldering or anisotropic conductive film (ACF) bonding which use a combination of pressure, heat, and time. In an embodiment, the transducer 28 may, without limitation, comprise a sixty-four (64) element linear phased array comprised of piezoelectric composite (PZT) materials. In an embodiment, the transducer 28 may be housed in silicone. In an embodiment, the transducer 28 may be visible with or under fluoroscopy.

In an exemplary embodiment, the ultrasound transducer assembly 12 may have a transducer 28 having sixty-four (64) piezoelectric elements and four flexible printed circuits 30 operatively or conductively connected to the transducer 28. Each of the four flexible printed circuits 30 may, for example, include eighteen (18) traces 38 and eighteen (18) pads 40, wherein each individual trace $38_N$ may be operatively or conductively connected to each individual pad $40_N$, creating a trace/pad circuit. In such an embodiment, eighteen (18) conductive traces $38_{1-18}$ and eighteen (18) conductive pads $40_{1-18}$ may form eighteen (18) trace/pad circuits, wherein two (2) trace/pad circuits may be connected to ground wires, and the remaining sixteen (16) trace/pad circuits may be connected to sixteen (16) piezoelectric elements of the transducer 28. In an exemplary embodiment, the two outermost trace/pad circuits may correspond to ground wiring, and the sixteen (16) inner trace/pad circuits may correspond to 16 separate piezoelectric elements. For example, and without limitation, piezoelectric elements one (1) through sixteen (16) may correspond with a first flexible printed circuit $30_1$, piezoelectric elements seventeen (17) through thirty-two (32) may correspond with a second flexible printed circuit $30_2$, piezoelectric elements thirty-three (33) through forty-eight (48) may correspond with a third flexible printed circuit $30_3$, and piezoelectric elements forty-nine (49) through sixty-four (64) may correspond with a fourth flexible printed circuit $30_4$. While the ultrasound transducer assembly 12 has been described with four flexible printed circuits $30_{1-4}$, the present disclosure is not meant to be so limited. Rather, a plurality of flexible printed circuits $30_N$ may be used as required and remain with the spirit and scope of the present disclosure.

Figure 4:
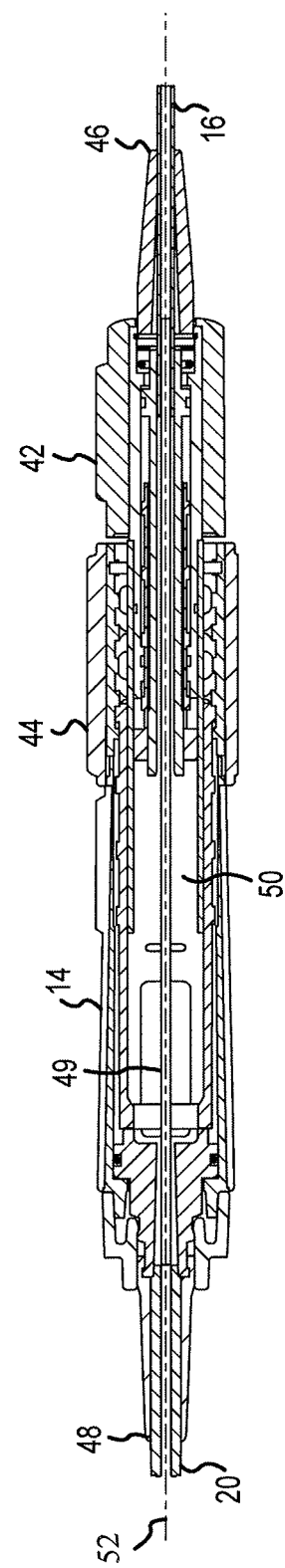
FIG. 4 is an illustration of a cross-sectional side view of an embodiment of the handle of FIG. 1

As generally illustrated in FIGS. 1, 2, and 4, an embodiment of the handle 14 may be similar to a handle described in U.S. application Ser. No. 13/105,646 (published as United States patent application publication no. 2011/0282176 A1 on 17 Nov. 2011), which is incorporated by reference in its entirety as though fully set forth herein. In embodiments, the handle 14 may provide for four-way steering of the distal end portion of the body 16 of the catheter 10 (described in further detail below) and/or the ultrasound transducer assembly 12 by manipulation of two or more control members. As seen in FIG. 2, embodiments of the handle 14 may include an actuator or knob 42 or a plurality of actuators or knobs, such as a first knob 42 and a second knob 44, which may be configured to manipulate two or more control members. As seen in FIG. 4, the handle 14 may have a distal end 46 and a proximal end 48. The wire harness 18, located in a lumen of the body 16, may enter the distal end 46 of the handle 14, pass internally through the handle 14 via a passage 50, and exit the proximal end 48 of the handle 14. In an embodiment, a portion of the wire harness 18 may be surrounded by a protective sleeve 49 in the passage 50 of the handle 14. After the wire harness 18 passes through the handle 14, the wire harness 18 may pass into a lumen of the tubing 20. In an embodiment, the wire harness 18 may directly pass through the passage 50 in the handle 14 along a path substantially parallel to a central longitudinal axis 52 of the handle 14. In another embodiment, a portion of the wire harness 18 may be provided off-center of the handle 14 when the wire harness 18 exits the proximal end of the handle 14.

As generally illustrated in FIGS. 1 and 2, the body 16 of the catheter 10 may comprise a flexible tubular body 16 having a deflectable distal end portion 54 and a proximal end 56. The deflection of the distal end portion 54 of the body 16 may be actuated by the handle 14 and the deflection of distal end portion 54 may be multi-directional. In an embodiment, the distal end portion 54 of the body 16 may be configured for four-directional deflection allowing for left-right and posterior-anterior deflection, with an angle of at least about 120 degrees in each direction. In an embodiment, the distal end portion 54, which may be deflectable, may be approximately four and one-half (4½) inches in length. In another embodiment, the deflectable length may be approximately 11.68 cm±0.50 cm. In an embodiment, the distal end portion 54 of the body 16 may be deflected in a posterior-anterior direction, for example, by rotating the first knob 42 located on the handle 14. In an embodiment, the anterior/posterior deflection may be separated from each other by 180 degrees nominal and ±25 degrees from a plane described by a neutral indicator on the handle 14 and a center axis of the distal end portion 54 of the body 16. In an embodiment, the distal end portion 54 of the body 16 may also be deflected in a left-right deflection by rotating the second knob 44 located on the handle 14. In an embodiment, the left-right deflection may be separated from each other by 180 degrees nominal and ±25 degrees from the plane described by the neutral indicator on the handle 14 and a center axis of the distal end portion 54 of the body 16. In another embodiment, the first knob 42 may control the left-right deflection and second knob 44 may control the posterior-anterior direction. In an embodiment, the body 16 may be cylindrical and electrically non-conductive. In an embodiment, the body 16 may have a 9 French (F) diameter. In an embodiment where the body 16 has a 9 F diameter, a 10 F introducer may for example be used with the 9 F body for insertion into the femoral or jugular veins. In an embodiment, the body 16 may comprise a radio-opaque Pebax™ tubing. In an embodiment, the body 16 may have a usable length ("L1") of about 90 cm. In an embodiment, the ultrasound transducer assembly 12 may be located at the distal end portion 54 of the body 16 and the wire harness 18 (such as for example described in further detail below) attached to the ultrasound transducer assembly 12 may extend through the body 16 from substantially the distal end 24 to the proximal end 26 of the catheter 10. In an embodiment, the body 16, and the wire harness 18 extending through the body 16, may enter an opening of the handle 14.

As previously described, the wire harness 18 may pass completely through the handle 14, such that the handle 14 is between a distal end 58 of the wire harness 18 and a proximal end 60 of the wire harness 18. In an embodiment, the portion of the wire harness 18 between the handle 14 and proximal end 60 of the wire harness 18 may be covered by the tubing 20. In an embodiment, the tubing 20 may be connected to the connector 22 and the handle 14, and the tubing 20 may protect and package the wire harness 18. In an embodiment, the tubing 20 and the wire harness 18 extending through the tubing 20, such as shown in FIG. 2, may have a length ("L2") that may be about 110 cm long.

Referring to FIGS. 5-10, the wire harness 18 may comprise a wiring bundle 62, a distal flex circuit 64, and a proximal flex circuit 66. The wire harness 18 may be configured to electrically connect an ultrasound transducer assembly 12 to the electrical control unit (ECU) 23, wherein the ECU 23 may control various functions of the transducer 28, including but not limited to, capturing and recording signal data obtained from the transducer 28, and providing images based on transducer 28 data via a display device 27 connected to the ECU 23.

Figure 5:
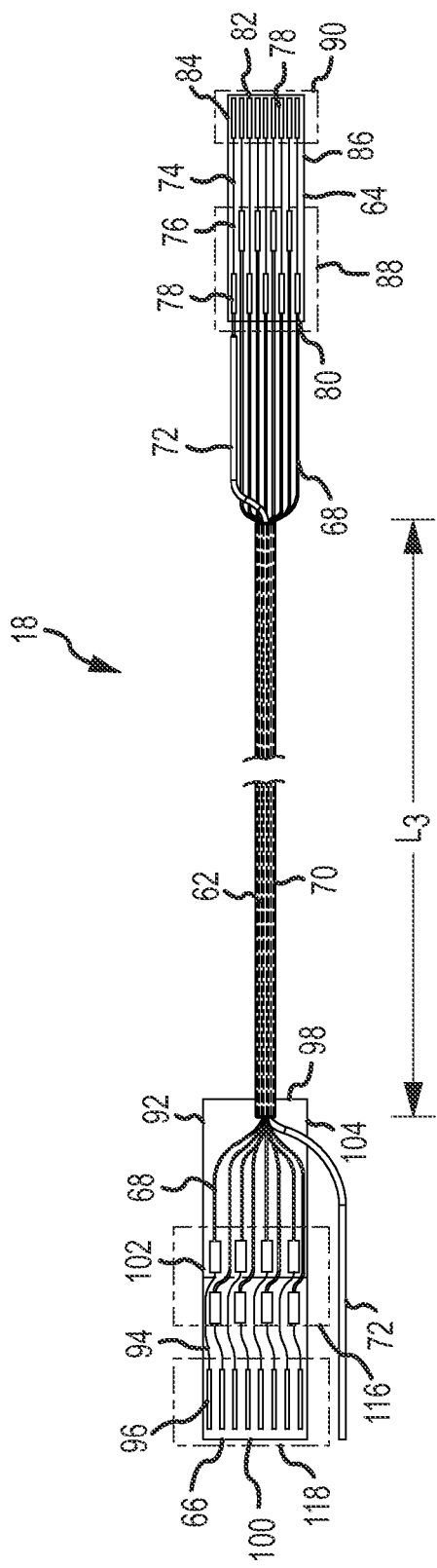
FIG. 5 is an illustration of an embodiment of a wire harness.
Figure 6:
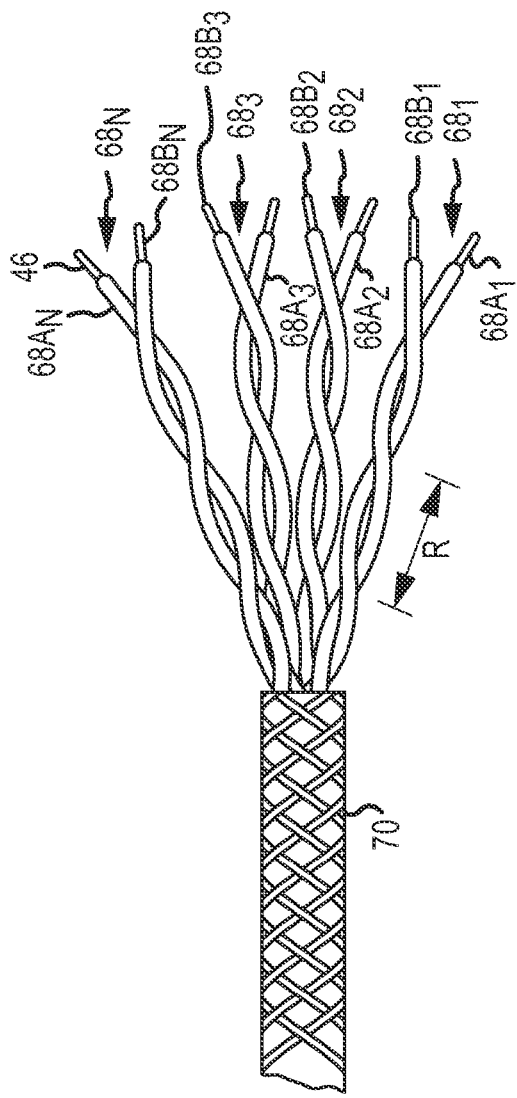
FIG. 6 is a general illustration of an embodiment of a plurality of twisted pair wiring.

The wiring bundle 62 may have a distal portion and a proximal portion. The wiring bundle 62 of the wire harness 18 may comprise a plurality of twisted pair wiring 68 (or twisted wire pairs) and a shield 70, as shown in FIGS. 5 and 6. As generally illustrated in FIG. 6, each twisted pair wiring may comprise two wires 68A, 68B with insulation surrounding each individual wire 68A, 68B. The two individual wires 68A, 68B may then be twisted around each other, forming the twisted pair wiring 68. The rate or frequency of twisting ("R") may, for example and without limitation, be 27 turns per inch. In an exemplary embodiment, the wires 68A, 68B may be forty-six (46) gauge wiring and each individual wire 68A, 68B may be color coded, wherein the color may be predefined to connect to a particular circuit. In an exemplary embodiment, the plurality of twisted pair wiring 68 may be bound together in a straight lay routing orientation, where each twisted pair wiring 68 is not twisted around another twisted pair wiring 68. A straight lay routing orientation may provide benefits, such as minimizing the cross-sectional diameter of the wiring bundle 62 and/or maximizing the flexibility of the wiring bundle 62. In an exemplary embodiment, the plurality of twisted pair wiring 68 may comprise eight twisted pair wirings 68. The plurality of twisted pair wiring 68 bound together may be secured with the shield 70. In an exemplary embodiment, the shield 70 may be braided and may have a pigtail wire 72 running throughout the length of the shield 70. In an exemplary embodiment, the shield 70 may comprise a silver plated copper braiding. In an exemplary embodiment, the shield 70 may be forty-six (46) gauge. In an exemplary embodiment, the shield 70 may cover at least 90% of the length of the plurality of twisted pair wiring 68. For some embodiments, the shield 70 may have a length ("L3") as much as 100 inches or more. In an exemplary embodiment, one end of the shield 70 may be located approximately one-half inch (½ inch) from an edge 80 of the distal flex circuit 64 and the other end of the shield 70 may be located approximately one-half inch (½ inch) from an edge 98 of the proximal flex circuit 66.

As generally illustrated in FIGS. 5 and 10, the distal flex circuit 64 of the wire harness 18 may be a flexible printed circuit 30 comprising a flexible substrate 74, a plurality of conductive traces 76, and a plurality of conductive pads 78.

The substrate 74 may have a generally thin thickness (cross-sectional area) which may allow the substrate 74 to flex, bend, and fold. The shape of the substrate 74 may be defined by a first edge 80, a second edge 82, a third edge 84, and a fourth edge 86. The first edge 80 (or proximal edge) may be located closest to the end of the shield 70 of the wiring bundle 62. The second edge 82 (or distal edge) may be located opposite the first edge 80. The third and fourth edges 84, 86 may be each adjacent the first and second edges 80, 82, and the third and fourth edges 84, 86 may each connect to the first and second edges 80, 82. In an embodiment, the substrate 74 may be substantially rectangular in shape, where the shape is defined by the first edge 80, second edge 82, third edge 84, and fourth edge 86. In an embodiment, the substrate 74 may comprise a dielectric material, such as, but not limited to, polyimide.

The plurality of conductive traces 76 and the plurality of conductive pads 78 may be defined on the substrate 74. Predetermined traces 76 and pads 78 may be combined, creating trace/pad combinations configured to create electrically conductive circuits on the flexible circuit. The pads 78 may be generally larger in width than the traces 76. In an embodiment, the pads 78 may be configured for receiving a solder joint to connect a particular wire to a particular circuit created trace/pad combination. In another embodiment, the pads 78 may be configured to mate to a corresponding set of pads 78 located on one of the plurality of flexible printed circuits 30 of the ultrasound transducer assembly 12. In an embodiment, the electrically conductive bond between the distal flex circuit 64 of the wire harness 18 and the flexible printed circuit 30 of the ultrasound transducer assembly 12 may be connected using reflow (hot bar) soldering. In another exemplary embodiment, an anisotropic conductive film (ACF) may be used for the electrically conductive bond by placing the ACF between the distal flex circuit 64 of the wire harness 18 and the flexible printed circuit 30 of the ultrasound transducer assembly 12.

In an exemplary embodiment, the distal flex circuit 64 may have two sets of conductive pads 78, a first set 88, and a second set 90. Each set 88, 90 may have a plurality of conductive pads 78 where the number of pads 78 in a set is equal to the number of defined electrical circuits on the distal flex circuit 64. For example, in an exemplary embodiment, the first set 88 may have nine pads 78, and the second set 90 may have nine pads 78. Each pad 78 in the set 88, 90 may be part of a defined circuit connected by the traces 76. In other words, the first pad 78 in the first set 88 may be connected to the first pad 78 in the second set 90, wherein each pad 78 is connected by the traces 76. Thus, the embodiment having nine pads 78 per set 88, 90 would have nine separate circuits. While the description above describes sets 88, 90 having nine pads 78, it will be appreciated that the present disclosure is not meant to be so limited. Rather, other exemplary embodiments may use any number of pads 78 per set to accommodate the desired amount of electrical circuits. Accordingly, it will be appreciated that embodiments other than those described with particularity herein remain within the spirit and scope of the present disclosure.

In an exemplary embodiment, a first set of pads 78 may be attached to the twisted pair wiring 68 of the wire bundle 62 and the pigtail wiring 72 of the shield 70. For example, in an embodiment having a wiring bundle 62 with eight twisted pair wiring 68, each set of pads 78 on the distal flex circuit 64 may have nine pads 78. One wire 68A from each of the eight twisted pair wiring 68 may be soldered, or connected via other bonding techniques, to a corresponding pad 78 of the first set 88. The other wires 68B of the twisted pair wirings 68, not directly connected to the first set 88, may be operatively or conductively connected to the pigtail wiring 72 of the shield 70, and the pigtail wiring 72 may then be operatively or conductively connected to a ninth pad 78 of the first set 88. In an embodiment, the ninth pad 78 may be used for grounding purposes. In an embodiment, after the twisted pair wiring 68 has been connected to either the first set 88 or the pigtail wiring 72, the connection may be covered with a nonconductive material, such as, but not limited to, epoxy, which may protect the connection. The second set of pads 90, located near the second edge 82 of the substrate 74, may be used to operatively or conductively connect to the flexible printed circuit 30 of the ultrasound transducer assembly 12 using the techniques described above, such as, but not limited to, reflow (hot bar) soldering or ACF. While the above embodiment describes a wire harness 18 using eight twisted pair wiring 68 connected to nine circuits defined on the distal flex circuit 64, any number of twisted pair wiring 68 may be utilized to accommodate the required amount of circuits defined on the distal flex circuit 64 and remain within the spirit and scope of the present disclosure.

The proximal flex circuit 66 of the wire harness 18 may be a flexible printed circuit 30 comprising a flexible substrate 92, a plurality of conductive traces 94 defined on the substrate, and a plurality of conductive pads 96 as generally illustrated in FIG. 6.

The substrate 92 may have a generally thin thickness (cross-sectional area) which may allow the substrate 92 to flex, bend, and/or fold. The shape of the substrate may be defined by a first edge 98, a second edge 100, a third edge 102, and a fourth edge 104. The first edge 98 (or distal edge) may be located closest to the end of the shield 70 of the wiring bundle 62. The second edge 100 (or proximal edge) may be located opposite the first edge 98. The third and fourth edges 102, 104 may be each adjacent the first and second edges 98, 100, and the third and fourth edges 102, 104 may each connect to the first and second edges 98, 100. In an embodiment, the substrate 92 may be generally rectangular in shape. In an embodiment, the substrate 92 may comprise a dielectric material, such as, but not limited to, polyimide.

The plurality of traces 94 and the plurality of pads 96 may be defined on the substrate 92. Predetermined traces 94 and pads 96 may be combined, creating trace/pad combinations configured to create electrically conductive circuits on the flexible circuit. The pads 96 may have a generally larger width than the traces 94. In an embodiment, the pads 96 may be configured for receiving a solder joint to connect a particular wire 68A to a particular circuit created by the trace/pad combination.

Figure 7:
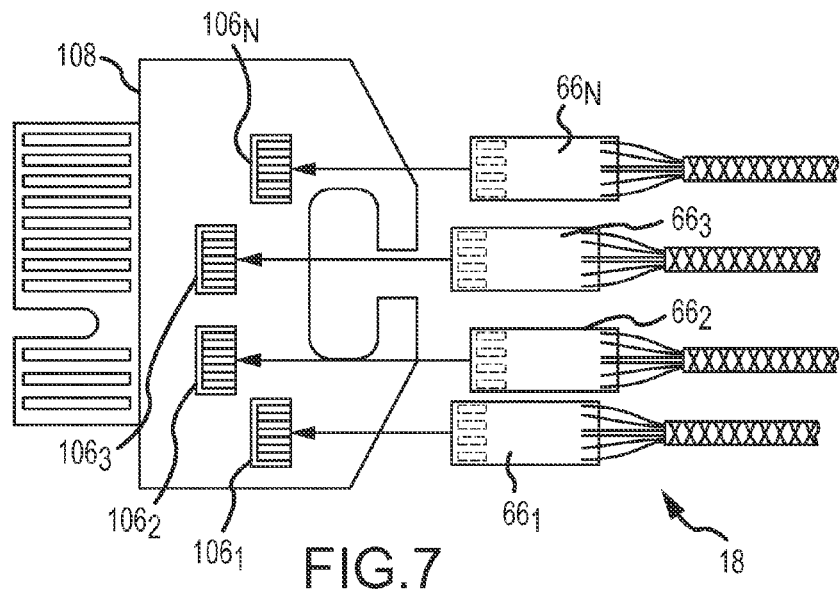
FIG. 7 is an illustration of an embodiment of an electrical connector having a plurality of zero insertion force (ZIF) connectors configured to receive a plurality of wire harnesses.
Figure 8:
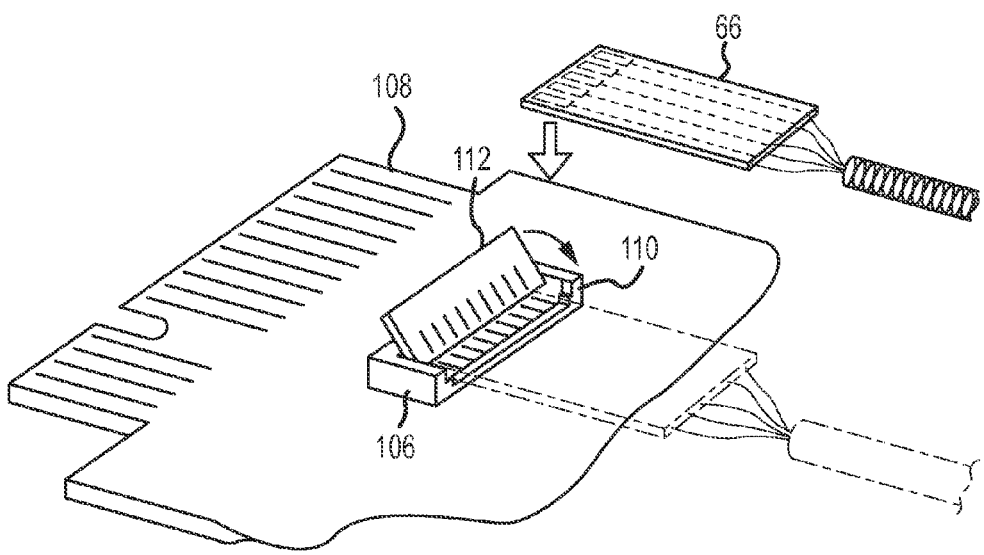
FIG. 8 is an illustration of the ZIF connector of FIG. 7, configured to receive a proximal end of the wire harness of FIG. 5.

As generally illustrated in FIGS. 7-8, another embodiment of the pads 96 and substrate 92 of the proximal flex circuit 66 may be configured to mate to at least one zero insertion force (ZIF) connector 106 located on a printed circuit board 108, such as a cable edge card, of the electrical connector 22. The ZIF connector 106 may be configured to receive the proximal flex circuit 66. The pads 96 located on the substrate 92 of the proximal flex circuit 66 may be placed directly inside or on a first portion 110 of the ZIF connector 106. A second portion 112 of the ZIF connection 106 may engage the first portion 110 of the ZIF connection 106, causing a conductive connection between the ZIF connector 106 and the proximal flex circuit 66, as well as physically gripping of the substrate 92 of the proximal flex circuit 66. An advantage associated with some ZIF connection systems is that the system does not require a mating half to be fitted to the flexible printed circuit 30, such as the proximal flex circuit 66, which can save space and cost of reduced or miniaturized equipment. In an embodiment, the printed circuit board 108 (such as a rigid cable edge card) having at least one ZIF connector 106 may be configured to electrically connect to the ECU 23. The printed circuit board (such as a rigid cable edge card) may be located in a housing 114 of the electrical connector 22. The electrical connector 22 may connect to the ECU 23.

As seen in FIGS. 5, 9, and 10, embodiments of the proximal flex circuit 66 may have two sets of pads 96, a first set 116 and a second set 118. Each set 116, 118 may have a plurality of pads where the number of pads 96 in a set 116, 118 matches the number of defined electrical circuits on a proximal flex circuit 66. For example, in an embodiment, the first set 116 may have eight pads 96 and the second set 118 may also have eight pads 96. Each pad 96 in the set 116, 118 may be part of a defined circuit connected by the traces 94. In other words, the first pad 96 in the first set 116 may be connected to the first pad 96 in the second set 118, wherein each pad 96 is connected by a trace 94. Thus, an embodiment having eight pads 96 per set 116, 118 may, for instance, have eight separate circuits.

In an embodiment, a first set 116 of pads 96 may be attached to twisted pair wiring 68 of a wire bundle 62. For example, without limitation, in an embodiment having a wiring bundle 62 with eight twisted pair wiring 68, the first set 116 of pads 96 on the proximal flex circuit 66 may have eight pads 96. One wire 68A from each of the eight twisted pair wiring 68 may be soldered, or attached via other electrically connected bonding techniques, to a corresponding pad 96 of the first set 116. The other wires 68B of the twisted pair wirings 68, not directly connected to the first set 116 of pads 96, may be connected to the pigtail wiring 72 of the shield 70, and may then be wrapped and not connected to the proximal flex circuit 66. The pigtail wiring 72 combined with the other wires 68B of the twisted pair wirings 68 located by the proximal end 60 of the wire harness 18 may be secured to the shield 70. In an embodiment, after the twisted pair wiring 68A has been connected to the first set 116 of pads 96, the connection may be covered with a nonconductive material, such as, but not limited to, epoxy, which may protect the connection. The second set 118 may be located near the second edge 100 and the proximal flex circuit 66 with the second set 118 of pads 96 may be inserted into the ZIF connector 106 located on the printed circuit board 108. In an embodiment, the printed circuit board 108 may be connected to, for example, a St. Jude Medical ViewFlex™ Catheter Interface Module which may be connected to a St. Jude Medical ViewMate™ Z or ViewMate™ II intracardiac ultrasound console. While the above embodiment describes a wire harness 18 using eight twisted pair wiring 68 connected to eight circuits defined on the proximal flex circuit 66, any number of twisted pair wiring 68 may be utilized to accommodate the required amount of circuits defined on the proximal flex circuit 66.

The various embodiments of the wire harness 18 described above discloses a singular wire harness 18 electrically connecting the ultrasound transducer assembly 12 to the electrical connector configured to electrically connect to the ECU 23. It will be appreciated, however, that a plurality of wire harnesses 18 may be used to electrically connect the ultrasound transducer assembly 12 to the ECU 23 as seen in FIG. 3. There may be various benefits to using a plurality of wire harnesses 18, including without limitation, maximizing flexibility of the medical device using the wire harnesses 18, reduced size of the flex circuits for packaging the wire harness 18 in the catheter 10, and utilizing economies of scale by using common wire harnesses 18 on different medical devices.

For example, and without limitation, in the previously described embodiment of an ultrasound transducer assembly 12 having sixty-four (64) piezoelectric elements and four flexible printed circuits 30 electrically connected to the transducer 28, each of the four flexible printed circuits 30 may have eighteen (18) separate circuits for a total of seventy-two (72) circuits (sixty-four (64) circuits to electrically conduct the signal between the piezoelectric elements and ECU 23 and eight ground circuits). Eight separate wire harnesses 18 may be used to connect the ultrasound transducer assembly 12 to the ECU 23, two wire harnesses 18 per flexible printed circuit 30 of the ultrasound transducer assembly 12.

As seen in FIGS. 9 and 10, embodiments of the flexible printed circuit 30 of the ultrasound transducer assembly 12 may have the ground circuits located on the outermost circuits. These embodiments may allow the first and second wire harness 18A, 18B to match the position of the outermost ground circuits of the ultrasound transducer assembly 12 when connecting the wire harnesses 18A, 18B to the ultrasound transducer assembly 12. The first wire harness 18A and the second wire harnesses 18B may differ only in the location of the ground circuit on the distal flex circuit 64. For example, as seen in FIG. 9, the distal flex circuit may have a plurality of circuits created by the combination of the traces $76_{1-N}$ and pads $78_{1-N}$ (e.g., trace/pad circuits $76_{1-N}$, $78_{1-N}$). The first wire harness 18A may have a ground circuit $76_{GND}$, $78_{GND}$ located adjacent the first trace/pad combination $76_1$, $78_1$. As seen in FIG. 10, the second wire harness 18B may have the ground circuit $76_{GND}$, $78_{GND}$ located adjacent the $N^{th}$ trace/pad combination $76_N$, $78_N$. In both the first and second wire harnesses 18A, 18B, the ground circuit may be one of the outermost trace/pad circuits. In an embodiment, the two wire harnesses 18 may be color coded. For example, the first wire harness 18A may be color coded red and the second wire harness 18B may be color coded black.

As seen in FIG. 3, in an embodiment where two wire harnesses 18 are attached to each flexible printed circuit 30 of the ultrasound transducer assembly 12, each flexible printed circuit 30 of the ultrasound transducer assembly 12 may be folded over onto itself along a fold line 120 oriented generally parallel to at least a portion of the traces 38. By folding the flexible printed circuit 30 of the ultrasound transducer assembly 12, the width ("$W_1$") of the flexible printed circuit 30 of the ultrasound transducer assembly 12 may be reduced to a smaller width ("$W_2$"), which may be approximately the same width ("$W_3$") as the distal flex circuits 64 of the wire harnesses 18. Use of the various embodiments of the wire harnesses 18 disclosed herein, may provide the benefit of improved and/or consistent flexibility of the body 16 when maneuvered in multiple directions by the control handle 14.

Although only certain embodiments have been described above with a certain degree of particularity, those skilled in the art could make numerous alterations to the disclosed embodiments without departing from the scope of this disclosure. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. Additionally, the terms "electrically connected" and "in communication" are meant to be construed broadly to encompass both wired and wireless connections and communications. It is intended that all matter contained in the above description or shown in the accompanying drawings shall be interpreted as illustrative only and not limiting. Changes in detail or structure may be made without departing from the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A wire harness for a medical device comprising an elongate body with a lumen, the wire harness comprising:
   a wiring bundle comprising:
      a distal portion and a proximal portion;
      a plurality of twisted pair wiring;
      a common ground wire, wherein one wire from each of said plurality of twisted pairs is electrically and physically coupled with the common ground wire; and
      a shield surrounding a portion of the plurality of twisted pair wiring;
   a distal flex circuit connected to the distal portion of the wiring bundle, the distal flex circuit configured to operatively connect to an electrically controlled object; and
   a proximal flex circuit connected to the proximal portion of the wiring bundle, the proximal flex circuit configured to operatively connect to an electrical connector;
   wherein the common ground wire is electrically coupled with at least one of the distal flex circuit or the proximal flex circuit;
   wherein the wire harness is sized and configured to extend substantially through the lumen of the elongate body of the medical device.

2. The wire harness of claim 1, wherein the plurality of twisted pair wiring are provided in a straight lay orientation.

3. The wire harness of claim 1, wherein the electrically controlled object is an ultrasound transducer assembly comprising an ultrasound transducer and a plurality of flexible printed circuits, and the distal flex circuit is configured to operatively connect to at least one of the plurality of flexible printed circuits.

4. The wire harness of claim 3, wherein the ultrasound transducer comprises at least sixty-four piezoelectric elements.

5. The wire harness of claim 3, wherein the operative or conductive connection between the distal flex circuit and the at least one of the plurality of flexible printed circuits is bonded or soldered.

6. The wire harness of claim 3, wherein the operative connection between the distal flex circuit and the at least one of the plurality of flexible printed circuits is bonded with anisotropic conductive film provided between the distal flex circuit and the at least one of the plurality of flexible printed circuits.

7. The wire harness of claim 1, wherein the proximal flex circuit comprises a flexible substrate and a plurality of conductive pads, and the flexible substrate and the plurality of conductive pads are configured to connect to a zero insertion force (ZIF) type connector.

8. The wire harness of claim 7, wherein the ZIF type connector is provided on a rigid printed circuit board.

9. The wire harness of claim 1, wherein the medical device comprises a handle, and wherein the wire harness is configured to extend completely through the handle.

10. The wire harness of claim 1, wherein the medical device comprises a handle including at least one actuator, wherein the at least one actuator is configured such that manipulation of the at least one actuator steers the elongate body in at least four directions.

11. The wire harness of claim 1, wherein the wiring bundle comprises at least eight twisted pair wiring.

12. The wire harness of claim 1, wherein the twisted pair wiring has a twist rate of at least 27 turns per inch.

13. The wire harness of claim 1, wherein the shield comprises a silver plated copper braiding.

14. The wire harness of claim 1, wherein the shield comprises a pigtail wire and the pigtail wire comprises the common ground wire, the twisted pair wiring comprises a first wire and a second wire, and the proximal flex circuit comprises a flexible substrate and a plurality of conductive pads, and wherein the first wire of the twisted pair wiring is operatively terminated on a separate conductive pad of the plurality of conductive pads, and the second wire is operatively connected to the pigtail wire.

15. The wire harness of claim 1, wherein the shield comprises a pigtail wire and the pigtail wire comprises the common ground wire, the twisted pair wiring comprises a first wire and a second wire, and the distal flex circuit comprises a flexible substrate and a plurality of conductive pads, and wherein the first wire of the twisted pair wiring is operatively terminated on a separate conductive pad of the plurality of conductive pads, the second wire is operatively connected to the pigtail wire, and the pigtail wire is operatively terminated on a conductive pad of the plurality of conductive pads.

16. The wire harness of claim 15, wherein the electrically controlled object comprises at least one flexible printed circuit comprising a set of conductive pads, and wherein the distal flex circuit has a set of conductive pads provided proximate a distal end of the distal flex circuit, wherein the set of conductive pads have not been directly connected to a first wire of the twisted pair wiring, and wherein the set of conductive pads of the distal flex circuit are configured to conductively bond to the set of conductive pads of the electrically controlled object.

17. A pair of wire harnesses for a medical device comprising a first wire harness and a second wire harness, each wire harness comprising:
   a wiring bundle comprising:
      a plurality of twisted pair wiring; and
      a shield surrounding a portion of the plurality of twisted pair wiring, the shield of the first wire harness being separate from the shield of the second wire harness;
   a distal flex circuit configured to operatively connect to an electrically controlled object assembly comprising an electrically controlled object and at least one flexible printed circuit, wherein the electrically controlled object assembly is provided in a distal portion of the medical device; and
   a proximal flex circuit configured to operatively connect to an electrical connector;

wherein the wiring bundle operatively connects the distal flex circuit to the proximal flex circuit, and wherein the first wire harness and the second wire harness are each operatively connected to the same flexible printed circuit of the electrically controlled object assembly.

18. The wire harness of claim 17, wherein the electrically controlled object comprises at least one flexible printed circuit comprising a flexible substrate having a first width, and wherein the flexible substrate of the electrically controlled object is configured to bend or fold to a second width, and the second width is smaller than the first width.

19. A plurality of wire harness pairs for a medical device comprising:
- a wire harness pair comprising a first wire harness and a second wire harness, wherein each wire harness comprises:
  - a wiring bundle comprising:
    - a plurality of twisted pair wiring; and
    - a shield surrounding a portion of the plurality of twisted pair wiring, the shield for the first wire harness being separate from the shield for the second wire harness;
  - a distal flex circuit configured to operatively connect to an ultrasound transducer assembly comprising:
    - an ultrasound transducer; and
    - a plurality of flexible printed circuits operatively connected to the ultrasound transducer;
    - wherein the ultrasound transducer assembly is located in a distal portion of the medical device; and
  - a proximal flex circuit configured to operatively connect to an electrical connector configured to operatively connect to an electronic control unit;
  - wherein the wiring bundle operatively connects the distal flex circuit to the proximal flex circuit; and
  - wherein the first wire harness and the second wire harness are each operatively connected to the same flexible printed circuit of the plurality of flexible printed circuits of the ultrasound transducer assembly.

20. The wire harness of claim 19, wherein the plurality of wire harness pairs comprises at least four wire harness pairs.

* * * * *